(12) United States Patent
Davila et al.

(10) Patent No.: US 9,700,405 B2
(45) Date of Patent: Jul. 11, 2017

(54) DIRECTIONAL TISSUE EXPANDER

(71) Applicant: Mentor Worldwide LLC, Santa Barbara, CA (US)

(72) Inventors: Luis Alberto Davila, Alpharetta, GA (US); Anita M. Falcon, Bedford, TX (US); Krasimira Hristov, Belle Mead, NJ (US); Leo B. Kriksunov, Ithaca, NY (US); Robert J. Tannhauser, Bridgewater, NJ (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 144 days.

(21) Appl. No.: 14/230,251

(22) Filed: Mar. 31, 2014

(65) Prior Publication Data

US 2015/0272722 A1  Oct. 1, 2015

(51) Int. Cl.
*A61F 2/12* (2006.01)

(52) U.S. Cl.
CPC ........ *A61F 2/12* (2013.01); *A61F 2250/0003* (2013.01); *A61F 2250/0018* (2013.01)

(58) Field of Classification Search
CPC .......................................................... A61F 2/12
See application file for complete search history.

(56) References Cited

U.S. PATENT DOCUMENTS

| | | | |
|---|---|---|---|
| 4,671,255 A | 6/1987 | Dubrul et al. | |
| 4,863,470 A | 9/1989 | Carter | |
| 5,026,394 A | 6/1991 | Baker | |
| 5,447,535 A | 9/1995 | Muller | |
| 5,496,367 A | 3/1996 | Fisher | |
| 5,496,370 A | 3/1996 | Hamas | |
| 6,605,116 B2 | 8/2003 | Falcon et al. | |
| 6,743,254 B2 | 6/2004 | Guest et al. | |
| 8,192,486 B2 | 6/2012 | Glicksman | |
| 8,394,118 B2 | 3/2013 | Jones et al. | |
| 8,506,627 B2 | 8/2013 | Van Epps et al. | |
| 2007/0233273 A1 | 10/2007 | Connell | |
| 2009/0198331 A1 | 8/2009 | Kesten et al. | |
| 2009/0254179 A1 | 10/2009 | Burnett | |
| 2011/0208302 A1 | 8/2011 | Glicksman | |
| 2011/0230964 A1 | 9/2011 | Yacoub et al. | |
| 2011/0301706 A1 | 12/2011 | Brooks et al. | |
| 2012/0226352 A1* | 9/2012 | Becker | A61F 2/12 623/8 |

(Continued)

FOREIGN PATENT DOCUMENTS

| | | |
|---|---|---|
| EP | 0197726 B1 | 1/1992 |
| EP | 0963180 B1 | 10/2003 |

(Continued)

*Primary Examiner* — Katrina Stransky
*Assistant Examiner* — Wade P Schutte

(57) ABSTRACT

An expandable mammary implant including a shell having an anterior face and a posterior face. The anterior has an upper pole portion and a lower pole portion meeting at an apex, and an injection zone for receiving fluid therethrough to inflate the implant. A reinforcement material is coupled to the shell in a reinforcement zone. The reinforcement material is coupled to the shell so as to at least coincide with the upper pole portion and a peripheral rim portion that extends from the posterior face upwardly into said anterior face by a predetermined distance.

14 Claims, 8 Drawing Sheets

(56) References Cited

U.S. PATENT DOCUMENTS

| 2014/0077411 | A1 | 3/2014 | Schuessler et al. |
| 2014/0088702 | A1 | 3/2014 | Manesis et al. |
| 2015/0250574 | A1* | 9/2015 | Egnelov ................ A61F 2/0063 606/151 |

FOREIGN PATENT DOCUMENTS

| EP | 2387971 A1 | 11/2011 |
| GB | 2021954 A | 12/1979 |
| WO | WO 96/40003 A1 | 12/1996 |
| WO | WO 2004/103196 | 12/2004 |
| WO | WO 2008/154125 A1 | 12/2008 |
| WO | WO 2010/049926 A2 | 5/2010 |
| WO | WO 2011/058550 A1 | 5/2011 |

\* cited by examiner

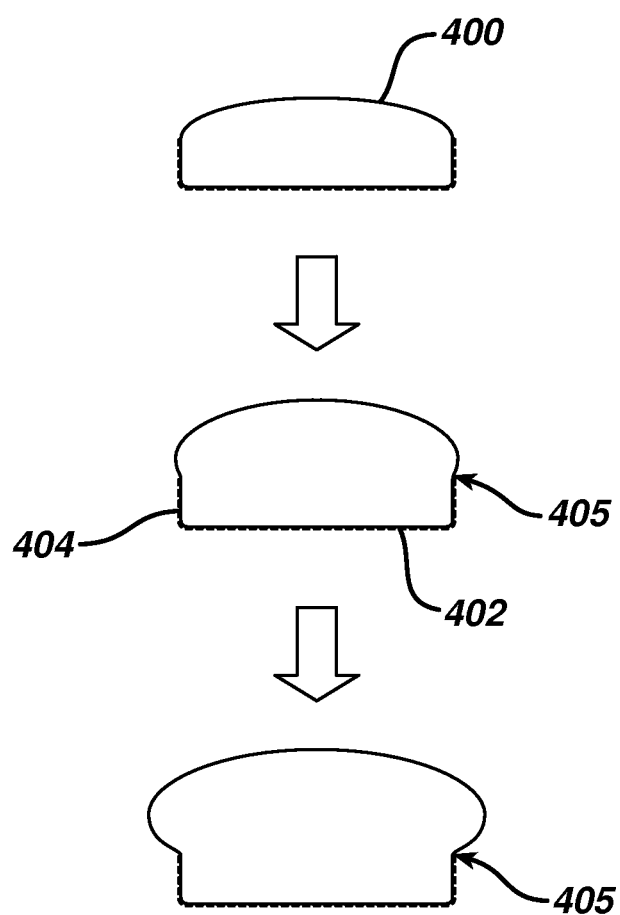

DIRECTIONAL TISSUE EXPANDER

FIELD OF THE INVENTION

The present invention relates generally to the field of expandable implants, and more particularly to expandable mammary implants.

BACKGROUND

Tissue expanders are devices that are implanted beneath the skin and then gradually inflated to stretch the overlying tissue. Such expanders are used to create a pocket for receiving a permanent prosthesis and/or to generate increased skin surface area so that skin can be utilized for grafting or reconstruction.

In the case of mammary implants, tissue expanders are used to create the mammary pocket that will ultimately receive the permanent mammary implant. These expanders are commonly formed of a silicone polymer shell. After implantation, saline or some other fluid is periodically injected into the expander over time, for example through an injection port, until the desired sized pocket is achieved.

With known mammary tissue expanders, as the inflation process continues, resistive pressure from the tissue on the anterior side of the expander can cause the expander to expand in undesired directions (i.e., axially and laterally). In order to minimize the undesired expansion, most surgeons select a smaller expander than needed and overinflate the expander to 200-300% of the rated volume of the expander. This allows the surgeon to utilize the smaller starting foot print of a smaller expander to accommodate for the undesired axial and lateral expansion. Overinflating a smaller expander is undesirable for various reasons. Although expanders are technically tested up to twice their nominal inflation volume, 200-300% inflation could reduce the safety margin of the device. Further, since the footprint is small, at 200-300% inflation the inflated shape is not anatomically correct, but rather is more round or ball-like, which could lead to rotation or flipping over of the implant within the tissue pocket.

Thus, is would be desirable to provide an expandable mammary implant that better provides for the appropriate directional tissue expansion for any given size.

SUMMARY OF THE INVENTION

The present invention provides an expandable mammary tissue implant including a shell having an anterior face and a posterior face, with the anterior face having an upper pole portion and a lower pole portion meeting at an apex, and an injection zone for receiving fluid therethrough to inflate the implant. The implant further includes a reinforcing material coupled to the shell in a first reinforcement zone and a second reinforcement zone. The first reinforcement zone forms at least a peripheral rim portion that extends from a periphery of the posterior face upwardly into the anterior face by a predetermined distance, and a first end of the first reinforcement zone is located in the upper pole region of the anterior face. The second reinforcement zone extends from a first end that substantially abuts or overlaps the first end of the first reinforcement zone, and along at least a portion of the anterior face of the shell such that the entire upper pole of the shell is reinforced as between the first and second reinforcement zones.

In one embodiment, the first reinforcement zone further extends along the entire posterior face of the shell. The predetermined distance that the first reinforcement zone extends upwardly into the anterior face of the shell may vary around the periphery of the posterior face of the shell. In yet another embodiment, the second reinforcement zone extends along at least a portion of the anterior face of the shell to an apex of the shell.

The reinforcing material may be a mesh material, and may further be a polyester mesh. The shell may be made of silicone.

In yet another embodiment, the reinforcing material has varying elasticity properties at different locations, and may have an elasticity gradient in a predetermined direction.

According to yet another embodiment, the implant further includes at least one insert member positioned entirely within and extending across an interior of the shell, and coupled to an interior surface of the shell. The insert member may be sized and shaped so as to be coupled to the interior of the shell around an entire perimeter of the insert member, and may further be coupled to the interior of the shell in a location substantially adjacent to an upper periphery of the first reinforcement zone. Alternatively, the insert member may be sized and shaped so as to be coupled to the interior of the shell around a portion of a perimeter of the insert member, and have a cutout therein. The insert member may further include a plurality of apertures therethrough, and/or have an elasticity gradient in a predetermined direction.

According to yet another embodiment, the at least one insert member may be coupled to the interior surface of the shell at first and second ends thereof.

Also provided is an expandable mammary implant including a shell having an anterior face and a posterior face, with the anterior having an upper pole portion and a lower pole portion meeting at an apex, and an injection zone for receiving fluid therethrough to inflate the implant. The implant further includes a reinforcement material coupled to the shell in a reinforcement zone. The reinforcement material is coupled to the shell so as to at least coincide with the upper pole portion and a peripheral rim portion that extends from the posterior face upwardly into the anterior face by a predetermined distance.

In another embodiment, the reinforcement zone may further extend from the upper pole portion along the anterior face by a predetermined distance, with the predetermined distance being less than or equal to the distance to the apex of the shell. The reinforcement zone may further coincide with the entire posterior face of the shell. In yet another embodiment, the predetermined distance that the first reinforcement zone extends upwardly into the anterior face of the shell varies around the periphery of the posterior face of the shell.

According to yet further alternate embodiments, the reinforcing material may be a mesh material, such as a polypropylene mesh, and the shell may be made of silicone.

In a further embodiment, the reinforcing material has varying elasticity properties at different locations, and may have an elasticity gradient in a predetermined direction.

An insert member may further be included that is positioned entirely within and extends across an interior of the shell, and is coupled to an interior surface of the shell. It may be sized and shaped so as to be coupled to the interior of the shell around an entire perimeter of the insert member, and may further be coupled to the interior of the shell in a location substantially adjacent to an upper periphery of the first reinforcement zone.

The insert member may further include a plurality of apertures therethrough, and/or have an elasticity gradient in a predetermined direction.

Alternatively, the insert member may be a strip coupled to the interior surface of the shell at first and second ends thereof.

The present invention also provides an expandable mammary tissue implant including a shell having an anterior face and a posterior face, with the anterior face having an upper pole portion and a lower pole portion meeting at an apex, and an injection zone for receiving fluid therethrough to inflate the implant. The implant further includes a reinforcing material coupled to the shell in a reinforcement zone, wherein the reinforcement zone covers the upper pole and a peripheral zone extending from the peripheral rim of the posterior face into the anterior face such that upon inflation, expansion of the implant occurs disproportionately in the lower pole region.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 4a is an exemplary illustration of a possible transition zone between reinforced and non-reinforced portions of a shell;

DETAILED DESCRIPTION

Figure 1:
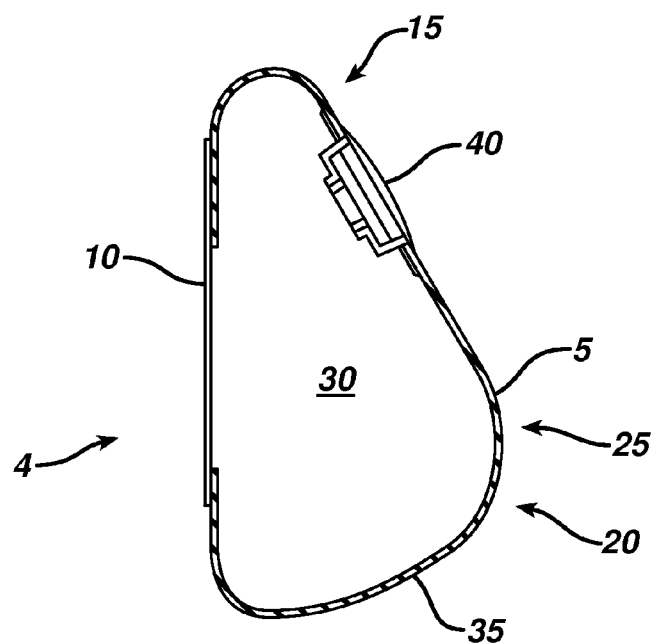
FIG. 1 is a cross-sectional side view an exemplary prior art mammary tissue implant.

FIG. 1 shows a cross-sectional side view of an exemplary prior art mammary tissue expander 4. The expander has a posterior face 10 that lies substantially flat and is placed against a patient's chest wall, and an anterior face 5 that faces outward from the chest wall when implanted. The anterior face 5 includes an upper pole region 15 (i.e., the upper portion of the shell when the implant recipient is standing), a lower pole region 20 (i.e., the lower portion of the shell when the implant recipient is standing), and an apex 25 (corresponding to the point at which the nipple would be in a natural breast) separating the upper pole region and the lower pole region. The outer shell 35 of the expander 5 is typically made of a silicone material and includes an injection port or other valve or self-sealing zone 40 through which saline or another fluid is injected over time into the contained inner region 30. In this manner, the volume of the expander can be increased over time until the desired size pocket is achieved.

With known expanders such as that shown in FIG. 1, although the overall shape of the expander when fully inflated as shown is somewhat anatomically correct, it has been found that when in use within the body, expansion does not occur in an anatomically correct or desired manner. This is because the expander of FIG. 1 is shown in air, and known expanders are designed and tested in air. Due to the minimal resistance of the surrounding air, an expander with an outer shell comprised of a substantially uniform material will expand to the final shape of that shell. In the body, however, the surrounding tissue and muscles counteract expansion, and a device with a substantially uniform outer shell will expand according to the path of least resistance, often determined by the varying resistance of the surrounding tissue. For mammary prostheses, this typically results in deformity of the outer shell to a more pancake like shape, with the anterior projection of the lower pole expansion being less than planned or desired, and lateral and axial expansion more than desired. As indicated previously, in an effort to increase the anterior projection of lower pole expansion, surgeons often pick undersized expanders having a smaller footprint (as against the chest wall), and over inflate them.

The present invention overcomes the problems described above and provides for expansion in the appropriate direction in an appropriate sized implant. More specifically, the implants described herein allow for minimized lateral and vertical expansion, while providing a more anatomically correct profile with less fullness in the upper pole region and more fullness and anterior expansion in the lower pole region. As shown in the illustrative embodiment in FIG. 2, the implant of the present invention includes reinforcement at various locations along the shell to provide for minimal expansion at various desired locations and full expansion at other predetermined locations, to result in an expander that has desired and varied expansion characteristics around its surface area when in actual use within the body.

Figure 2:
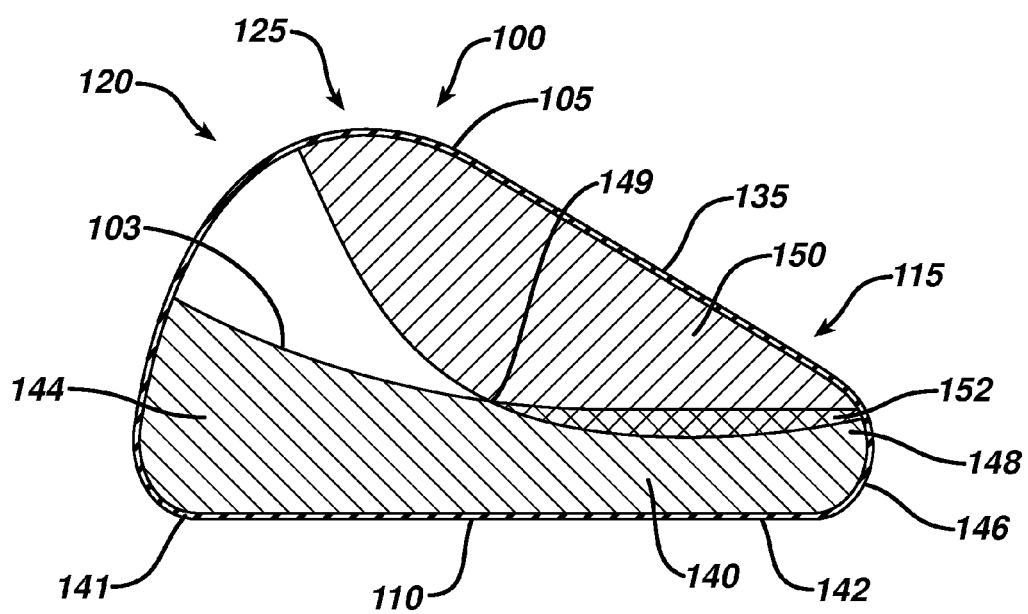
FIG. 2 is a side view of an exemplary mammary tissue implant according to the present invention.
Figure 3:
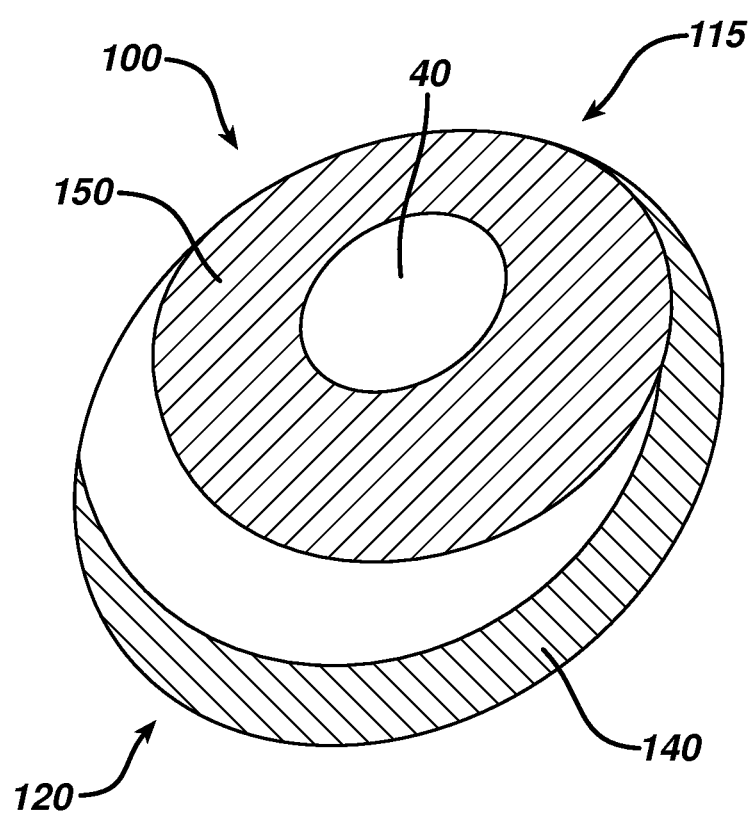
FIG. 3 is a perspective view of the device of FIG. 2.

The expander 100 of FIGS. 2 and 3 similarly includes a posterior face 110 and an anterior face 105 that includes an upper pole region 115, a lower pole region 120, and an apex 125. As indicated previously, the posterior face is substantially flat when the shell is inflated and is the portion of the shell that lies against the patient's chest wall. The posterior face is defined by periphery 141. The expander also includes an injection zone 40. The injection zone may be an injection dome of the well-known type as illustrated in FIG. 1, may be a self-sealing area, or any other suitable device/area through which fluid can be injected and/or removed from the implant.

The outer shell 135 of the expander 100 further includes one or more reinforcement zones, wherein a reinforcing material limits the expandability of the outer shell material. According to one embodiment, the outer shell is made of silicone, and the reinforcing material is a mesh, such as a polyester mesh, although any suitable implantable mesh may be used. Alternatively, the reinforcing material may be a silicone sheet having an elasticity equal to or lower than the elasticity of the shell. The area of the shell having a reinforcing material coupled to it will have an overall elasticity less than any unreinforced area regardless of the elasticity of the reinforcing material. In a preferred embodiment, however, the reinforcing material has elasticity that is substantially lower than the elasticity of the shell.

Further, any other suitable material may be used that adequately functions to restrict expansion of the shell by having an elasticity that is equal to or less than that of the shell material. Exemplary other materials include silicone based polymers, composite materials, polyurethane, polypropylene, and other biocompatible polymeric materials. The reinforcing material may be coupled to the shell by covering the mesh with an un-vulcanized silicone sheet and pressing it into the shell such that the un-vulcanized silicone sheet essentially acts as a glue. The strength of the formed connection can be improved by curing the silicone at an elevated temperature over a period of time (i.e., 315-350 degrees Fahrenheit for approximately 30 minutes).

The embodiment of FIG. 2 includes a first reinforcement zone 140 and a second reinforcement zone 150, both of which are illustrated with cross-hatching. The first reinforcement zone 140 has a first end 146 and a second end 144, and includes at least a peripheral rim portion 148 that extends from the periphery 141 of the posterior face 110 upward into the anterior face 105 by a predetermined distance to an upper periphery 103. The predetermined distance may be constant around the periphery, or may vary along the periphery as shown in FIG. 2. The first reinforcement zone may further extend so as to coincide with the entirety of the posterior face, or some portion thereof. The first reinforcement zone 140 restricts lateral and axial expansion of the shell in the peripheral area immediately adjacent to the posterior face. In this manner, the surgeon need not choose an expander having a smaller posterior face than desired in order to account for undesired lateral expansion around the perimeter of the base of the implant.

The embodiment of FIG. 2 further includes a second reinforcement zone 150. A first end 152 of the second reinforcement zone preferably substantially abuts or overlaps a first end 148 of the first reinforcement zone 140 so that the upper pole region 115 of the expander is entirely reinforced as between the first and second reinforcement zones. In this manner, upon being infused with fluid, the expander is unable to appreciably expand in the upper pole region. The second reinforcement zone extends from the first end 152 and along at least a portion of the anterior face region 105 of the expander, essentially forming a reinforced "hinge" like structure centered around the upper pole region 115, and having hinge points 149 on both sides where the first and second reinforcement zones first meet and start to overlap or abut each other. In certain embodiments, the reinforcement material covers from about 25% to about 80% of the shell surface area, and more preferably from about 50% to about 75% of the shell surface area.

In this manner, expansion of the upper pole region beyond the intended shape is restricted, while more freely allowing desirable expansion of the lower pole region 120. In one embodiment, the second reinforcement zone extends substantially to the apex 125 of the shell.

Although the embodiment above is described as having first and second pieces of reinforcing material, one skilled in the art will readily understand that the reinforcement zones can be established with a single piece as well.

In a further aspect of the present invention, the reinforcing material may be designed so that the degree of elasticity of the material varies at different locations. With a uniform reinforcing material, particularly when the elasticity of the reinforcing material is much different than that of the shell, it may be the case that somewhat sharp transition zones appear between the reinforced regions of the shell and the unreinforced regions. An exemplary illustration is shown in FIG. 4a, wherein the implant shell 400 is reinforced along the posterior face 402 and a peripheral region 404 similar to that described above. The difference in elasticity between the shell material and the reinforced zone may cause a sharp transition at the point 405 where the reinforced shell meets the unreinforced shell as demonstrated in FIG. 4a with an implant shell shown in three stages of inflation. To minimize this possible effect, the reinforcing material may have varying elasticity properties at different locations, or simply have an elasticity gradient (gradually decreasing or increasing elasticity properties) in a given direction. In a preferred embodiment, elasticity of the reinforcing material increases in the direction towards the areas which are free of reinforcing material, or have less reinforcing material, so that the reinforcing material immediately adjacent the non-reinforced areas has the highest elasticity. This can be accomplished by various means including, for example, providing apertures in the reinforcing material that vary in size and/or density along the length of the material. Exemplary embodiments are shown in FIGS. 5a-5c, with FIG. 5a illustrating circular apertures of varying diameter 500a along the length of the material, and FIGS. 5b and 5c illustrating varying slit-like aperture arrangements 500b, 500c along the length of the material. Further, the thickness of the mesh or other material may vary along the length to achieve this result. In another embodiment, both varying aperture size and/or aperture density (i.e., the number of apertures in a given area) along the length of the material and/or simultaneously varying thickness along the length of the material are contemplated to provide the desired elasticity gradient.

Figure 4B:
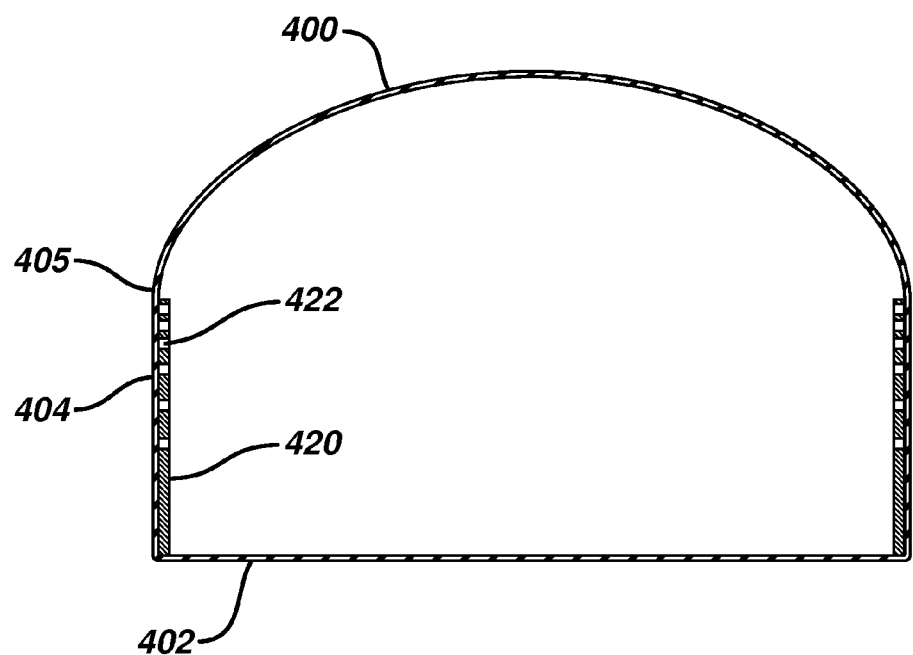
FIG. 4b illustrates the mammary implant of FIG. 3 further including a reinforcing material having varying elastic properties.
Figure 5A:
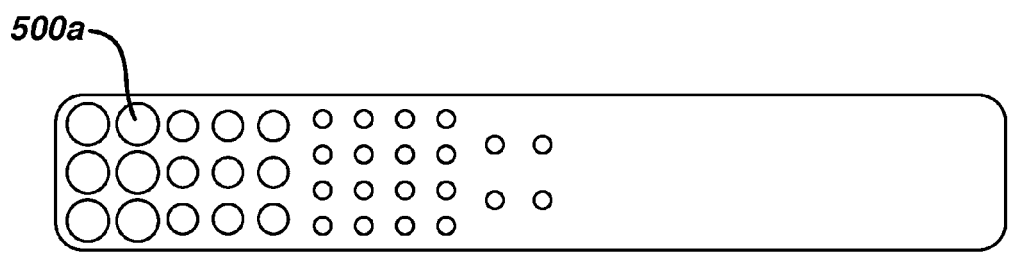
FIGS. 5a-5c illustrate exemplary embodiments of a reinforcing material having varying elastic properties along its length.
Figure 5B:
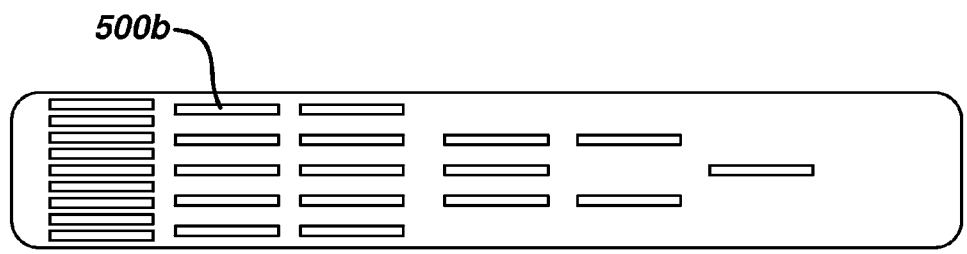
Figure 5C:
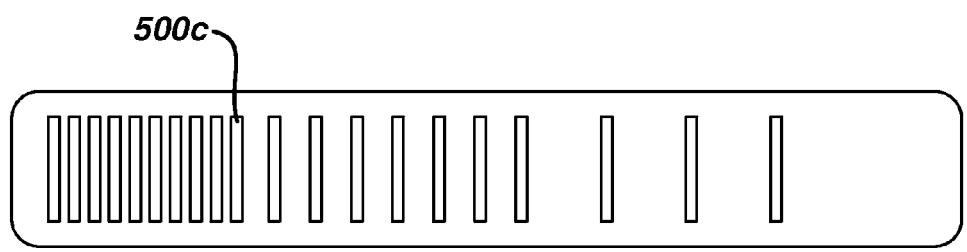

FIG. 4b illustrates the implant shell 400 having reinforcing zone 420 with a lower elasticity proximal to the posterior face 402 and a higher elasticity in the peripheral region 404, with elasticity increasing due to higher density of apertures 422 cut in the material 420. As can be seen from FIG. 4b, elasticity is higher closest to the transition point 405 where the reinforced shell meets the unreinforced shell.

Figure 6A:
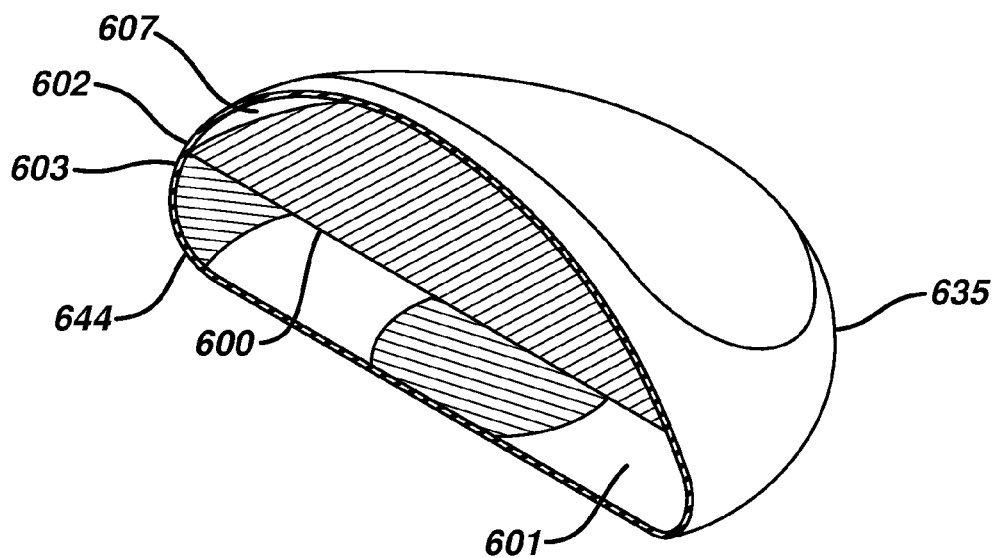
FIG. 6a is a cross-sectional, perspective view illustrating a mammary tissue implant according to the present invention including an insert member.
Figure 6B:
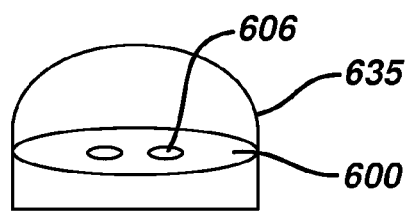
FIG. 6b illustrates an alternate configuration for a mammary implant having an insert member.

In yet another embodiment of the invention, the device illustrated in FIGS. 2 and 3 may further include an additional, separate reinforcing insert member 600 as illustrated in FIGS. 6a and 6b. The insert member is positioned entirely within the interior space 601 of the shell 635. In the illustrated embodiment, the insert member is sized and shaped to span the entire interior or the shell and is secured to the interior surface 607 of the shell around its entire periphery 602, preferably at a location substantially adjacent to the upper periphery 603 of the first reinforcement zone 644. The insert member helps minimize undesired effects at a transition zone of the type described above, and further assists in maintaining the desired shape of the implant during expansion. The insert member may further include holes, apertures or the like 606, as illustrated in FIG. 6b, in order to allow movement of fluid within the shell as it is expanded. In alternate embodiments, the insert member may be in the form more of a "tether" or the like, such as a strip (or multiple strips) extending across the interior of the shell at any desired location, rather than having a configuration that substantially spans the entire interior. The insert member may be formed of any suitable material having an elasticity that is suitable to increase the shell's resistance to outward expansion, such as Dacron™, polypropylene, Dacron™-silicone composite, etc. The insert member may be secured to the inside of the shell using un-vulcanized silicone sheeting and heat, silicone-based adhesives, solvent-based bonding, diffusion bonding, ultrasonic welding, laser-spot welding, and other techniques known to a skilled artisan.

Figure 6C:
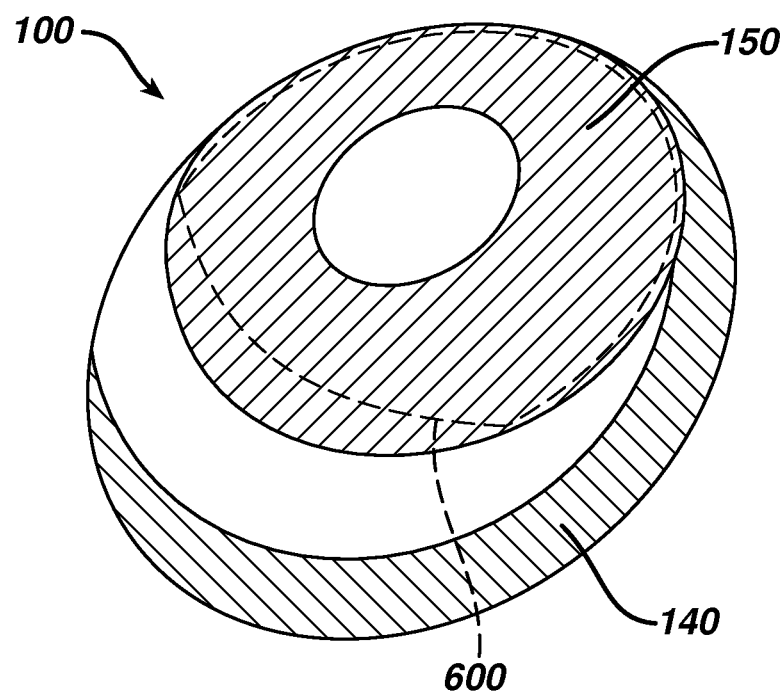
FIGS. 6c and 6d illustrate the mammary implant of FIG. 3 and further including an insert member.
Figure 6D:
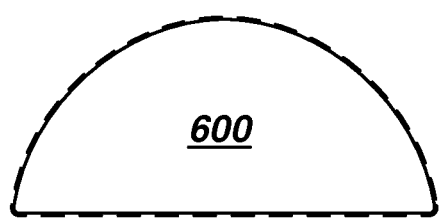

FIGS. 6c and 6d illustrate the implant of FIG. 3 having alternate insert member 600 therein. In this embodiment, the insert member (shown in dotted lines in FIG. 6c) is positioned in a substantially similar manner as illustrated in FIGS. 6a and 6b, but has an alternate "half-moon" type shape, as shown clearly in FIG. 6d.

Figure 6E:
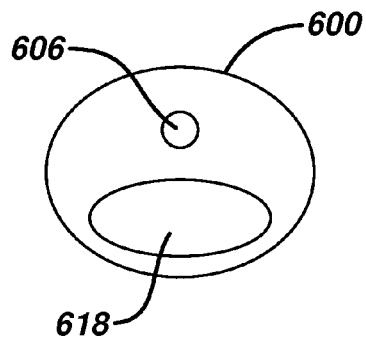
FIGS. 6e-6h illustrate various alternate embodiments of insert members.
Figure 6F:
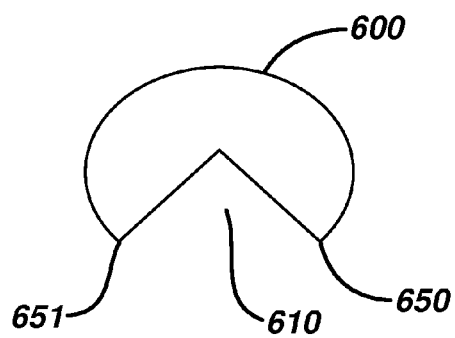
Figure 6G:
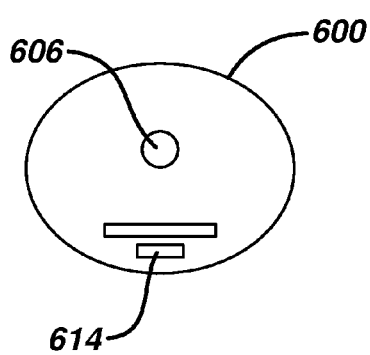

The reinforcing insert member 600 may have various other shapes and configurations, examples of which are shown in FIGS. 6e-6h. In FIG. 6f, the insert member 600 has a cutout 610 generally shaped/positioned so that its first and second points 650, 651 correspond to or substantially align with the hinges 149 where the first and second reinforcement zones begin to overlap (see FIG. 2). In FIG. 6e, the insert member 600 has a large size aperture 618 which is generally shaped/positioned so as to correspond to the location of the hinges. The size and location of large size aperture 618 are selected to locally increase elasticity of insert member 600, with area of the large size aperture 618 being from about 20% to about 40% of area of insert member 600, most preferably from about 20% to about 30% of area of insert member 600. FIG. 6g illustrates an insert member 600 with at least one optional aperture 606 and an array of slits 614 providing for increased elasticity of the insert member 600. The array 614 is generally shaped/positioned so as to correspond to the location of the hinges.

Figure 6H:
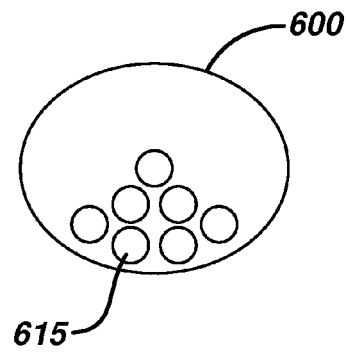

Finally, FIG. 6h illustrates an insert member 600 having a plurality of apertures 615 providing for increased elasticity of insert member 600, with apertures 615 generally shaped/positioned so as to correspond to location of hinge point as described previously.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. An expandable mammary tissue implant comprising:
    a shell having an anterior face and a posterior face having a periphery, the anterior face having an upper pole region and a lower pole region meeting at an apex, and an injection zone for receiving fluid therethrough to inflate the implant;
    a first reinforcing material having (i) a peripheral rim portion that extends from the periphery of said posterior face and (ii) an upper periphery, said first reinforcing material coupled to the shell such that the first reinforcing material does not extend along the entire anterior face, at least a portion of said first reinforcing material having a lower elasticity proximal to the posterior face and a higher elasticity towards the upper periphery;
    a second reinforcing material coupled to the shell and extending along a portion of the anterior face of the shell;
    wherein the first reinforcing material overlaps or abuts the second reinforcing material at or adjacent the upper periphery of the first reinforcing material in the upper pole region wherein a portion of the lower pole region is not reinforced by either the first or second reinforcing material.

2. The implant according to claim 1, wherein the first reinforcement material further extends along the entire posterior face of the shell.

3. The implant according to claim 1, wherein the peripheral rim portion of the first reinforcement material extends upwardly into the anterior face of the shell by a varying amount around the periphery of the posterior face of the shell.

4. The implant according to claim 1, wherein the second reinforcement material extends along at least a portion of the anterior face of the shell to or near the apex of the shell.

5. The implant according to claim 1, wherein the first and second reinforcing material is a mesh material.

6. The implant according to claim 5, wherein the mesh material is a polyester mesh.

7. The implant according to claim 1, wherein the shell is comprised of silicone.

8. An expandable mammary tissue implant comprising:
    a shell having an anterior face and a posterior face having a periphery, the anterior face having an upper pole region portion and a lower pole region meeting at an apex, and an injection zone for receiving fluid therethrough to inflate the implant;
    a first reinforcing material having (i) a peripheral rim portion that extends from the periphery of said posterior face and (ii) an upper periphery, said first reinforcing material coupled to the shell such that the first reinforcing material does not extend along the entire anterior face;
    a second reinforcing material coupled to the shell and extending along a portion of the anterior face of the shell;
    wherein the first reinforcing material overlaps or abuts the second reinforcing material at or adjacent the upper periphery of the first reinforcing sheet in the upper pole region, wherein a portion of the lower pole region is not reinforced by either the first or second reinforcing material; and
    at least one insert member positioned entirely within and extending across an interior of said shell, and coupled to an interior surface of said shell.

9. The implant according to claim 8, wherein the insert member is sized and shaped so as to be coupled to the interior of the shell around an entire perimeter of said insert member.

10. The implant according to claim 9, wherein the perimeter of the insert member is coupled to the interior of the shell in a location substantially adjacent to an upper periphery of said first reinforcement zone.

11. The implant according to claim 8, wherein the insert member is sized and shaped so as to be coupled to the interior of the shell around a portion of a perimeter of the insert member, and wherein the insert member has a cutout therein.

12. The implant according to claim 8, wherein the insert member has a plurality of apertures therethrough, and wherein the insert member has an elasticity gradient in a predetermined direction.

13. The mammary tissue expander according to claim 8, wherein said at least one insert member is a strip coupled to the interior surface of said shell at first and second ends thereof.

14. The implant according to claim 8, wherein the peripheral rim portion of the first reinforcement material zone extends upwardly into the anterior face of the shell by a varying amount around the periphery of the posterior face of the shell.

* * * * *